US010398827B2

(12) United States Patent
Pouchoulin

(10) Patent No.: US 10,398,827 B2
(45) Date of Patent: Sep. 3, 2019

(54) APPARATUS FOR EXTRACORPOREAL TREATMENT OF BLOOD AND METHOD OF CONTROL OF A BLOOD-WARMING DEVICE IN AN EXTRACORPOREAL BLOOD TREATMENT APPARATUS

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 338 days.

(21) Appl. No.: 15/510,302

(22) PCT Filed: Aug. 26, 2015

(86) PCT No.: PCT/EP2015/069497
§ 371 (c)(1),
(2) Date: Mar. 10, 2017

(87) PCT Pub. No.: WO2016/041745
PCT Pub. Date: Mar. 24, 2016

(65) Prior Publication Data
US 2017/0252501 A1 Sep. 7, 2017

(30) Foreign Application Priority Data
Sep. 15, 2014 (EP) .................................. 14184700

(51) Int. Cl.
A61M 1/36 (2006.01)
A61M 1/16 (2006.01)
(52) U.S. Cl.
CPC ............ *A61M 1/369* (2013.01); *A61M 1/166* (2014.02); *A61M 1/1629* (2014.02);
(Continued)

(58) Field of Classification Search
CPC .... A61M 1/1629; A61M 1/166; A61M 1/369; A61M 2205/3372; A61M 2205/505; A61M 2205/52
See application file for complete search history.

(56) References Cited

U.S. PATENT DOCUMENTS 4,894,164 A * 1/1990 Polaschegg ......... A61M 1/1656
210/646
6,626,857 B1 9/2003 Ohta et al.
(Continued)

FOREIGN PATENT DOCUMENTS

CN 2253204 4/1997
CN 102325555 1/2012

OTHER PUBLICATIONS

PCT International Search Report and Written Opinion for PCT/EP2015/069497 dated Oct. 14, 2015 (10 pages).
(Continued)

Primary Examiner — Benjamin J Klein
(74) Attorney, Agent, or Firm — Mueting, Raasch & Gebhardt, P.A.

(57) ABSTRACT

An extracorporeal blood treatment apparatus (1) comprising a control unit (10) connectable to a blood warming device (200). The apparatus (1) comprises: an extracorporeal blood circuit (100) and at least one infusion line (15, 21, 25) connected to the extracorporeal blood circuit (100). A control unit (10) is configured to execute the following procedure: receiving a first value representative of a desired blood temperature ($T_{des}$) at an end (70) of a blood return line (7) configured to be connected to a venous vascular access of a patient (P); receiving at least a first signal relating to at least a flow rate ($Q_{PBP}$, $Q_{REP1}$, $Q_{REP2}$) of an infusion fluid in the at least one infusion line (15, 21, 25); calculating a set point value of an operating parameter ($T_{OUT}$; $P_w$) to be imposed on the warming device (200) configured to heat a blood
(Continued)

heating zone (H) of the extracorporeal blood circuit (100) in order to maintain the desired blood temperature ($T_{des}$) at the end (70) of the blood return line (7). The set point is calculated based on input parameters comprising: at least the first value representative of the desired blood temperature ($T_{des}$) and at least one selected in the group of: the first signal ($Q_{REP1}$, $Q_{PBP}$, $Q_{REP2}$) and a second value representative of a temperature ($T_{REP1}$, $T_{PBP}$, $T_{REP2}$) of the at least one infusion fluid in the at least one infusion line (15, 21, 25).

15 Claims, 6 Drawing Sheets

(52) U.S. Cl.
CPC ............... *A61M 2205/3372* (2013.01); *A61M 2205/505* (2013.01); *A61M 2205/52* (2013.01)

(56) References Cited

U.S. PATENT DOCUMENTS

| | | |
|---|---|---|
| 8,834,720 B2 | 9/2014 | Ahrens |
| 2003/0218623 A1 | 11/2003 | Krensky |
| 2010/0000944 A1* | 1/2010 | Paolini .................... A61M 1/16 |
| | | 210/646 |

OTHER PUBLICATIONS

Office Action issued in China for Application No. 2015800496673 dated Aug. 6, 2018, 12 pages. (English translation attached).

\* cited by examiner

APPARATUS FOR EXTRACORPOREAL TREATMENT OF BLOOD AND METHOD OF CONTROL OF A BLOOD-WARMING DEVICE IN AN EXTRACORPOREAL BLOOD TREATMENT APPARATUS

This application is a U.S. National Stage Application of International Application No. PCT/EP2015/069497, filed Aug. 26, 2015, which was published in English on Mar. 24, 2016 as International Publication No. WO 2016/041745 A1. International Application No. PCT/EP2015/069497 claims priority to European Application No. 14184700.4 filed Sep. 15, 2014.

DESCRIPTION

The present invention relates to an apparatus for extracorporeal treatment of blood. In accordance with certain aspects, the extracorporeal treatment apparatus according to the invention is combined with, or comprises, a blood-warming device. The invention also concerns a method of control of a blood-warming device wherein the blood-warming device may be part of the extracorporeal blood treatment apparatus or may be a separate device, which is in communication with the extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and/or add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable fluid is removed from the blood by convection across the membrane into the secondary chamber. In a hemofiltration (HF) treatment, the blood flows past the semipermeable membrane as in UF (where waste and undesirable fluid are removed) and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the secondary chamber of the treatment unit. Undesirable matter from the blood crosses the semipermeable membrane into the secondary fluid by diffusion and desirable matter from the secondary fluid crosses the membrane into the blood. In a hemodiafiltration (HDF) treatment, blood and secondary fluid exchange matter as in HD, and, in addition, matter is added to the blood, typically by dispensing a fluid into the treated blood (infusion) either before and/or after it passes through the treatment unit and before its return to the patient as in HF.

During extracorporeal blood treatment therapies, the patient may loose significant amount of heat due to infusion fluids having lower temperature than blood, due to fluid exchange across the membrane of the treatment unit, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic HD or HDF, and in the case of low volume but continuous therapies like continuous renal replacement therapy (CRRT) (used in e.g. acute HD). Furthermore, the risk of hypothermia is even more problematic in case of treatments applied to low body weight patients, such as children.

Blood cooling due to fluid exchange (treatment and/or infusion fluids) is usually more important than heat losses to atmosphere in the complete extracorporeal blood circuit.

In order to prevent hypothermia during extracorporeal blood treatment several solutions have been developed in the past.

In accordance with a first known solution described in patent no. U.S. Pat. No. 4,894,164, the treatment fluid used for dialyzing blood is warmed-up in order to try to balance the heat lost by the blood circulating in the extracorporeal blood circuit. This solution presents however a number of drawbacks. Warming of treatment or infusion fluids requires managing fluid degassing, and may lead to precipitation problems when using bicarbonate solutions. Additionally, fluid warming requires multiplying the heating and degassing means on each fluid circuit when different fluid compositions are or have to be used (e.g. citrate anticoagulation).

In accordance with a second known solution, and in order to solve the above problems, blood warmers acting on the bloodline, and capable of directly warming blood, have been used. Blood warmers directly acting on the extracorporeal blood circuit have several benefits with respect to warming the treatment or the infusion fluid: in fact, blood warmers may be used with all types of therapies and do not cause problems of precipitation of solutes. Furthermore, as blood warmers act directly on the extracorporeal blood circuit it may be easier to control blood temperature. It should be noted that the blood warmers currently in the marketplace are formed by a device separate from the extracorporeal blood treatment apparatus and operating independently from this latter.

It is an object of the present invention according to at least some embodiments to improve management of the blood warming step in order to improve balancing of the cooling effects due in particular to infusion of fluids.

It is an object of the present invention according to at least some embodiments to render available an extracorporeal blood treatment apparatus capable of facilitating the control of patient temperature in extracorporeal blood circuits including infusion of fluids, in particular downstream of the warming device.

It is an object of the present invention according to at least some embodiments to provide an extracorporeal blood treatment apparatus and method capable of increasing patient safety.

It is an object of the present invention according to at least some embodiments to render available an extracorporeal blood treatment apparatus and method capable of efficiently cooperating with a warming device and providing improved management during the blood-warming step.

SUMMARY

Preferably at least one of the above objects is substantially reached by an apparatus or by an assembly according to one or more of the appended claims.

Preferably at least one of the above objects is substantially reached by a method according to one or more of below described aspects.

An apparatus and assemblies for the extracorporeal treatment of blood according to aspects of the invention are here below described.

A $1^{st}$ aspect relates to extracorporeal blood treatment apparatus, comprising:

an extracorporeal blood circuit having a treatment unit, a blood withdrawal line connected to a blood inlet of the treatment unit, and a blood return line connected to a blood outlet of the treatment unit;

a blood pump configured for controlling blood flow rate flowing through at least one of said blood withdrawal line and blood return line;

at least one infusion line connected to the extracorporeal blood circuit;

a control unit configured to execute the following procedure:

receiving a first value representative of a desired blood temperature at an end of the blood return line configured to be connected to a venous vascular access of a patient;

receiving at least a first signal relating to at least a flow rate of an infusion fluid in said at least one infusion line;

calculating a set point value of an operating parameter to be imposed on a warming device configured to heat a blood heating zone of the extracorporeal blood circuit in order to maintain said desired blood temperature at said end of the blood return line;

wherein the set point is calculated based on input parameters comprising:

at least the first value representative of the desired blood temperature and at least one selected in the group of:

the first signal and a second value representative of a temperature of said at least one infusion fluid in said at least one infusion line.

The invention allows to control the temperature of the blood flowing back into the patient and to keep it at the desired value without requiring any sensor placed at the end of the blood return line. In this way the overall structure of the apparatus and/or of the warming device does not require additional hardware with respect to the hardware already present on known apparatuses.

Indeed, the desired blood temperature is a value defined without the aid of any sensor of the apparatus but a pre-defined value for instance chosen by the physician. Such a desired blood temperature may be entered into the control unit of said apparatus though input devices (for instance a user interface). The desired blood temperature may be such to avoid any risk of hypothermia of the patient under treatment. The desired blood temperature may be substantially equal to the core temperature of the patient. The desired blood temperature may be a fixed value (by way of example such value may be 37.5° C.)

In a $2^{nd}$ aspect according to the previous aspect, the control unit is further configured to:

receive a second signal relating to the blood flow rate in the extracorporeal blood circuit;

wherein the input parameters comprise said second signal.

In a $3^{rd}$ aspect according to anyone of the previous aspects, the at least one infusion line is connected to the extracorporeal blood circuit at a junction point which is positioned downstream of the blood heating zone, in particular between the blood heating zone and said end of the blood return line.

In a $4^{th}$ aspect according to any one of the preceding aspects, the at least one infusion line comprises a post-infusion line directly connected to said blood return line.

The invention allows to keep the desired temperature of blood flowing back into the patient also if, as it usually happens, the most important cooling effect is due to infusion of fluid/s downstream of the warming device.

In a $5^{th}$ aspect according to any one of the preceding aspects, the at least one infusion line comprises a pre-infusion line directly connected to said blood withdrawal line.

In a $6^{th}$ aspect according to the preceding aspect, the pre-infusion line comprises a pre-blood pump infusion line directly connected to said blood withdrawal line upstream of said blood pump.

In a $7^{th}$ aspect according to the preceding aspect, the pre-infusion line is directly connected to said blood withdrawal line downstream of said blood pump.

The invention allows to keep the desired temperature of blood flowing back into the patient also in presence of a plurality of infusion lines downstream and/or upstream of the warming device.

In a $8^{th}$ aspect according to any one of the preceding aspects, said second value is a set or a measured value.

In a $9^{th}$ aspect according to any one of the preceding aspects, the second value is set by an operator via a user interface connected to the control unit.

In a $10^{th}$ aspect according to any one of the preceding aspects, said second value is representative of a room temperature where the apparatus is located.

The temperature of infusion fluids (usually contained in bags) may be taken equal to the room temperature (measured by means of a temperature sensor) or may be assumed equal to the Standard Temperature (25° C., SATP—standard ambient temperature and pressure).

In a $11^{th}$ aspect according to the preceding aspect, the apparatus comprises a room temperature sensor configured to measure the room temperature and to issue a corresponding measurement signal to the control unit.

In a $12^{th}$ aspect according to any one of the preceding aspects from $1^{st}$ to $7^{th}$, the apparatus comprises a fluid temperature sensor on said at least one infusion line, wherein the second value is a measured value detected by said fluid temperature sensor.

In a $13^{th}$ aspect according to the preceding aspect, the fluid temperature sensor is connected to the control unit and the control unit is configured to receive said measured value from said fluid temperature sensor.

In this case, the second value is more accurate thanks to the measured temperature of infusion fluid/s.

In a $14^{th}$ aspect according to any one of the preceding aspects, the apparatus comprises a treatment fluid line connected to the treatment unit.

In a $15^{th}$ aspect according to the preceding aspect, the control unit is further configured to:

receive a third signal relating to a flow rate of a treatment fluid in said treatment fluid line;

receive a third value representative of a temperature of said treatment fluid in said treatment fluid line;

wherein the input parameters also comprise the third signal and the third value representative of the temperature of the treatment fluid.

In a 16$^{th}$ aspect according to the preceding aspect, calculation of set point is performed taking into account characteristics of a filter of the treatment unit.

In a 17$^{th}$ aspect according to the preceding aspect, the apparatus comprises a plurality of infusion lines connected to the extracorporeal blood circuit, the control unit being configured for:
receiving a plurality of first signals, each relating to the flow rate of infusion fluid in a respective infusion line;
calculating said set point based on the following input parameters:
the first signal/s and
the temperature/s of the infusion fluid in the infusion line/s connected to the extracorporeal blood circuit downstream of the blood heating zone.

In a 18$^{th}$ aspect according to any one of the preceding aspects from 15$^{th}$ to 17$^{th}$, the blood heating zone is a portion of the extracorporeal blood circuit located in the blood withdrawal line, and wherein the control unit is configured for calculating said set point also based on the third signal and on the temperature of the treatment fluid.

In a 19$^{th}$ aspect according to any one of the preceding aspects from 15$^{th}$ to 18$^{th}$ the set point is calculated based on the following input parameters:
the first signal/s and on the temperature/s of the infusion fluid in the infusion line/s connected to the extracorporeal blood circuit upstream and downstream the blood heating zone and
the third signal and the temperature of the treatment fluid.

In a 20$^{th}$ aspect according to any one of the preceding aspects, the operating parameter is representative of the blood temperature at an outlet of the blood heating zone.

In a 21$^{st}$ aspect according to any one of the preceding aspects from 1$^{st}$ to 19$^{th}$, the operating parameter is a temperature of a part of the warming device, such as the temperature of a heating plate.

In a 22$^{nd}$ aspect according to any one of the preceding aspects from 1$^{st}$ to 19$^{th}$, the operating parameter is the electric power supplied to a heating unit of the warming device.

In a 23$^{rd}$ aspect according to any one of the preceding aspects, the blood heating zone is a portion of the extracorporeal blood circuit positioned on the blood return line.

In a 24$^{th}$ aspect according to any one of the preceding aspects from 1$^{st}$ to 22$^{nd}$, the blood heating zone is a portion of the extracorporeal blood circuit positioned on blood withdrawal line.

In a 25$^{th}$ aspect according to one of the preceding aspects from 1$^{st}$ to 22$^{nd}$, the blood heating zone is located at the treatment unit.

In a 26$^{th}$ aspect according to one of the preceding aspects from 1$^{st}$ to 14$^{th}$ and from 20$^{th}$ to 22$^{nd}$ and 25th, the warming device is located on the treatment fluid line. In this case, the warming device directly heats the treatment fluid and the treatment fluid heats the blood at the treatment unit.

In a 27$^{th}$ aspect according to one of the preceding aspects from 1$^{st}$ to 22$^{nd}$ and 24$^{th}$, the warming device is located on the blood withdrawal line.

In a 28$^{th}$ aspect according to one of the preceding aspects from 1$^{st}$ to 23$^{rd}$, the warming device is located on the blood return line.

In a 29$^{th}$ aspect according to one of the preceding aspects from 27$^{th}$ to 28$^{th}$, the warming device is configured to heat the blood heating zone.

In a 30$^{th}$ aspect according to one of the preceding aspects from 25$^{th}$ to 26$^{th}$, the warming device is configured to heat the treatment fluid line.

In a 31$^{st}$ aspect according to one of the preceding aspects, the apparatus comprises the warming device.

In a 32$^{nd}$ aspect according to one of the preceding aspects from 1$^{st}$ to 30$^{th}$, the blood warming device is separate from the apparatus.

In a 33$^{rd}$ aspect according to one of the preceding aspects, the warming device is connected to the control unit and the control unit is configured to generate a control signal comprising a command directed to impose to the warming device to operate with said operating parameter at the calculated set point.

In a 34$^{th}$ aspect according to the 32$^{nd}$ aspects, the control unit of the extracorporeal blood treatment apparatus is configured to communicate by means of a communication device (such as a display) the calculated set point value to an operator and the control system of the warming device is configured to receive said calculated set point value (by way of example entered by the operator by means of a user interface which may comprise buttons or knobs or a keyboard) and to impose to the warming device to operate with said operating parameter at the calculated set point.

In a 35$^{th}$ aspect according to one of the preceding aspects, the apparatus comprises a fluid temperature sensor configured to measure a blood temperature at the outlet of the blood heating zone and to issue a corresponding measurement signal.

In a 36$^{th}$ aspect according to the preceding aspect, the operating parameter is the blood temperature at the outlet of the blood heating zone.

In a 37$^{th}$ aspect according to the preceding aspect, the control unit is configured to perform a feedback control on the warming device, said feedback control comprising regulating electric power fed to a heating unit of the warming device based on a said measurement signal and on said calculated set point.

In a 38$^{th}$ aspect according to one of the preceding aspects, the apparatus comprises a communication device.

In a 39$^{th}$ aspect according to the preceding aspect, the control unit is configured to communicate by means of said communication device the set point to an operator.

In a 40$^{th}$ aspect according to one of the preceding aspects, the control unit is configured to recalculate the set point either periodically or when a change to at least one of the input parameters occurs.

In a 41$^{st}$ aspect according to one of the preceding aspects, the control unit is configured to compare the calculated set point with a maximum set point and to communicate said maximum set point by means of the communication device if the calculated set point exceeds the maximum set point.

In a 42$^{nd}$ aspect according to one of the preceding aspects, the control unit is configured to compare the calculated set point with a maximum set point and to impose to the warming device to operate at the maximum set point if the calculated set point exceeds the maximum set point.

In a 43$^{rd}$ aspect according to one of the preceding aspects, the control unit is configured to send a warning message about the patient over-warming risk by means of the communication device when infusion is stopped for a preset amount of time.

In a 44$^{th}$ aspect according to one of the preceding aspects, the control unit is configured to receive the patient weight and wherein the emission of the warning message also depends on said patient weight. In an aspect, the emission of the warning message also depends on the flow rate of blood.

In an aspect, the emission of the warning message also depends on the ratio between the blood flow rate and the patient weight.

In a 45th aspect according to one of the preceding aspects, the control unit receives or stores a function interrelating said set point with said input parameters and wherein calculation of the set point is performed using said function.

A 46th aspect concerns an assembly including the extracorporeal blood treatment apparatus and the warming device, wherein the warming device and the extracorporeal blood treatment apparatus are separate.

In a 47th aspect according to the preceding aspect, the warming device comprises a respective control system separate from the apparatus control unit.

In a 48th aspect according to the preceding aspect, the control system of the warming device is configured to receive from the control unit a control signal comprising a command directed to impose to the warming device to operate with said operating parameter at the calculated set point imposed by said command.

In a 49th aspect according to the preceding aspects from 46th to 48th, the warming device comprises a fluid temperature sensor configured to measure a blood temperature at the outlet of the blood heating zone and to issue a corresponding measurement signal.

In a 50th aspect according to the preceding aspect from 46th to 49th, the operating parameter is the blood temperature at the outlet of the blood heating zone.

In a 51st aspect according to the preceding aspect from 46th to 50th, the control system is configured to perform a feedback control, said feedback control comprising regulating electric power fed to a heating unit of the warming device based on a said measurement signal and on said calculated set point.

A 52nd aspect concerns a method of control a warming device in an extracorporeal blood treatment apparatus, wherein said apparatus comprises:
an extracorporeal blood circuit having a treatment unit, a blood withdrawal line connected to a blood inlet of the treatment unit, and a blood return line connected to a blood outlet of the treatment unit;
a blood pump configured for controlling blood flow rate flowing through at least one of said blood withdrawal line and blood return line;
at least one infusion line connected to the extracorporeal blood circuit;
wherein the method comprises:
calculating a set point value of an operating parameter to be imposed on a warming device configured to heat a blood heating zone of the extracorporeal blood circuit in order to maintain a desired blood temperature at an end of the blood return line configured to be connected to a venous vascular access of a patient;
wherein the set point is calculated based on input parameters comprising:
at least a first value representative of the desired blood temperature and
at least one selected in the group of:
a first signal relating to at least a flow rate of an infusion fluid in said at least one infusion line and
a second value representative of a temperature of said at least one infusion fluid in said at least one infusion line.

In a 53rd aspect according to one of the preceding aspects, the set point is calculated based also on blood properties (such as blood density, specific heat, hematocrit and/or total protein concentration).

In a 54th aspect according to one of the preceding aspects, the set point is calculated based also on heat losses to atmosphere in the extracorporeal blood circuit downstream of the blood heating zone.

DESCRIPTION OF THE DRAWINGS

Aspects of the invention are shown in the attached drawings, which are provided by way of non-limiting example, wherein.

DETAILED DESCRIPTION

Figure 1:
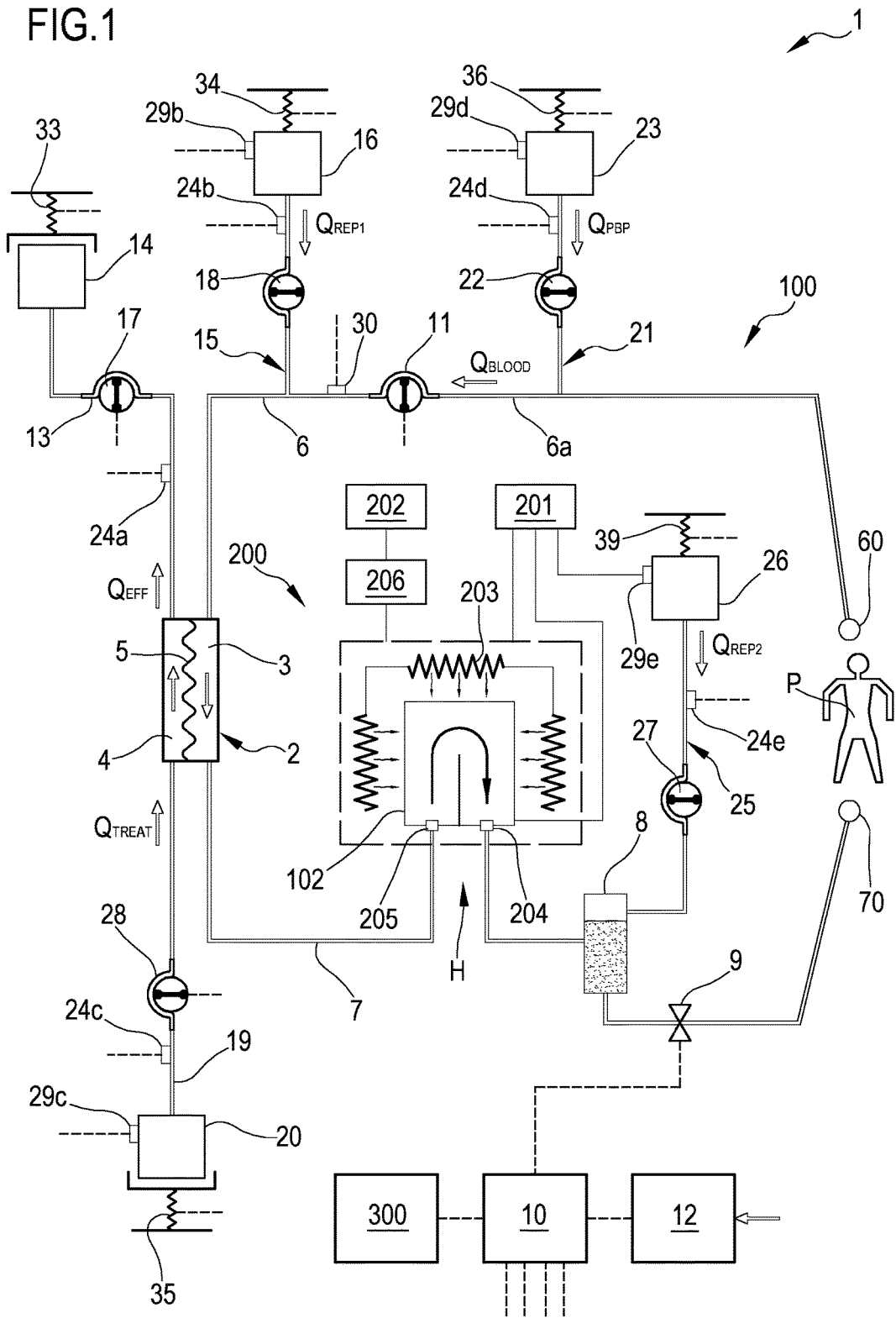
FIG. 1 schematically shows a first example of a blood treatment apparatus.
Figure 2:
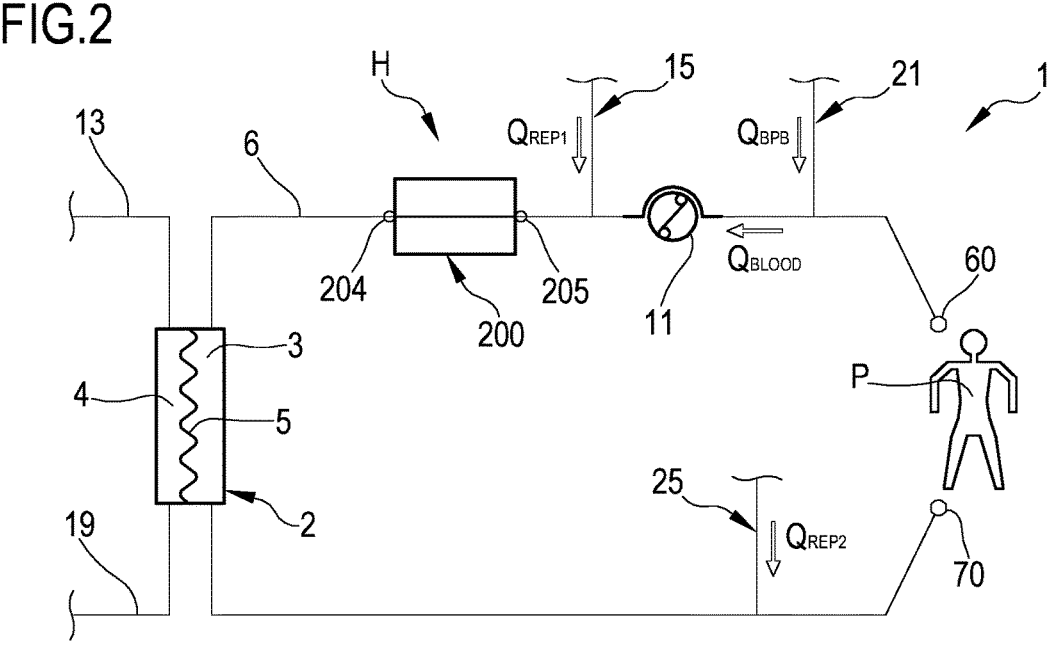
FIG. 2 schematically shows a second example of a blood treatment apparatus.
Figure 3:
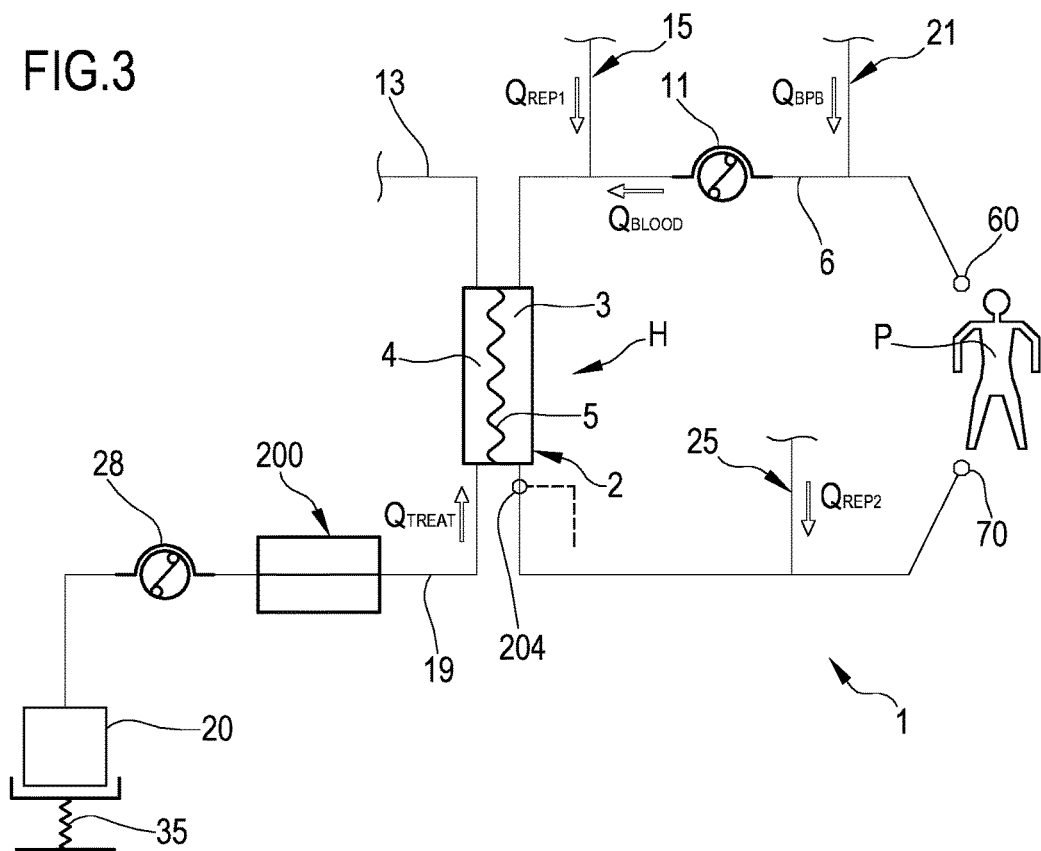
FIG. 3 schematically shows a third example of a blood treatment apparatus.

FIGS. 1 to 3 show exemplifying, and non limiting, embodiments of an apparatus for extracorporeal treatment of blood. Note that same components are identified by same reference numerals in FIGS. 1 to 3.

FIG. 1 schematically shows a first example of a blood treatment apparatus 1 designed for delivering any one of the following treatments: hemodialysis, hemofiltration, hemodiafiltration, and ultrafiltration.

The apparatus 1 comprises a treatment unit 2 having a primary chamber 3 and a secondary chamber 4 separated by a semipermeable membrane 5. Depending upon the treatment, the semipermeable membrane 5 of the treatment unit 2 may be selected to have different properties and performances. A blood withdrawal line 6 is connected to an inlet of the primary chamber 3, and a blood return line 7 is connected to an outlet of the primary chamber 3. The blood withdrawal line 6, the primary chamber 3 and the blood return line 7 are part of an extracorporeal blood circuit 100.

In use, an end 60 of the blood withdrawal line 6 is connected to a needle or to a catheter or other arterial access device (not shown) which is then placed in fluid communication with the vascular system of a patient P. An end 70 of the blood return line 7 is connected to a needle or to a catheter or other venous vascular access device (not shown) which is then placed in fluid communication with the vascular system of the patient P. Blood can be withdrawn through the blood withdrawal line 6, passed through the primary chamber 3 and then returned to the patient's vascular system through the blood return line 7.

An air separator, such as a bubble trap 8 may be present in the blood return line 7. Moreover, a safety clamp 9 controlled by a control unit 10 may be present on the blood return line 7 downstream the bubble trap 8. A bubble sensor (not shown), for instance associated with the bubble trap 8 or coupled to a portion of the line 7 between the bubble trap 8 and the safety clamp 9, may be present. If present, the bubble sensor is connected to the control unit 10 and sends to the control unit 10 signals for the control unit 10 to cause closure of the safety clamp 9 in case one or more bubbles above certain safety thresholds are detected.

As shown in FIG. 1, the blood flow rate $Q_{BLOOD}$ through the blood lines is controlled by a blood pump 11, for instance a peristaltic blood pump, acting either on the blood withdrawal line 6 (as shown in FIG. 1) or on the blood return line 7. An operator may enter a set value for the blood flow rate $Q_{BLOOD}$ by means of a user interface 12, and the control unit 10, during treatment, may be configured to control the blood pump 11 based on the set blood flow rate. The control unit 10 may comprise a digital processor (CPU) and memory (or memories), an analog circuit, or a combination thereof.

Blood flow rate through the extracorporeal blood circuit may be determined using a blood flow sensor 30.

An effluent fluid line 13 is connected, at one end, to an outlet of the secondary chamber 4 and, at another end, to a waste, for instance comprising an effluent fluid container 14 collecting the fluid extracted from the secondary chamber 4 or coming from a drainage line, not shown. The embodiment of FIG. 1 also presents a pre-infusion line 15 having one end connected to the blood withdrawal line 6. This line 15 supplies infusion fluid from an infusion fluid source, such as an infusion fluid container 16, connected at the other end of the pre-infusion line 15.

Note that alternatively or in addition to the pre-infusion line the apparatus 1 of FIG. 1 may include a post-infusion line 25 which may be connected to the blood return line 7 at a junction point (either at the bubble trap 8 or upstream the bubble trap 8 or even downstream the bubble trap 8 (e.g. upstream safety clamp 9). The post-infusion line 25 connects an infusion fluid source, such as a post-infusion fluid container 26 (which for instance may contain a drug, or calcium when performing citrate anticoagulation, or a nutrient solution or other), to the blood return line.

As mentioned, the apparatus 1 of FIG. 1 may include both a pre-infusion line 15 and a post-infusion line 25. In this case, each infusion fluid line may be connected to a respective infusion fluid container 16, 26, or the two infusion fluid lines may receive infusion fluid from a common source of infusion fluid such as one and the same infusion fluid container. Additionally, the apparatus 1 may present a further infusion line 21 connected, at one end, with a portion 6a of the blood withdrawal line 6 positioned upstream the blood pump 11 and, at its other end, with a further infusion fluid container 23, which for instance may contain a drug, or a regional anticoagulant such as a citrate solution or other. This further infusion line is herein referred to as pre-blood pump infusion line 21. The apparatus 1 of FIG. 1, may further include a treatment (dialysis) fluid line 19 connected at one end with a treatment (dialysis) fluid container 20 and at its other end with the inlet of the secondary chamber 4 of the treatment unit 2.

Although the exemplifying apparatus 1 shown in FIG. 1 comprises all lines 13, 19, 15, 21 and 25, this should not be read in a limitative manner. In fact the apparatus 1 may be of the type having only one or more of the above described infusion lines 15, 21, 25.

Depending upon the type of apparatus 1, and thus depending upon the number and type of lines present, corresponding pumps may be present or not. An effluent fluid pump 17 operates on the effluent fluid line 13 under the control of said control unit 10 to regulate the effluent fluid flow rate $Q_{EFF}$ in the effluent fluid line 13. If the apparatus 1 has a pre-infusion line 15, then a pre-infusion pump 18 acts on pre-infusion line 15 to regulate the pre-infusion flow rate $Q_{REP1}$ through the same pre-infusion line 15. If the apparatus 1 has a post-infusion line 25, then a post-infusion pump 27 acts on post-infusion line 25 to regulate the post-infusion flow rate $Q_{REP2}$ through the same post-infusion line 25. Note that in case of two infusion lines (pre-infusion 15 and post-infusion 25) each infusion line may cooperate with a respective infusion pump 18, 27.

In case the apparatus 1 has the treatment fluid line 19, a treatment fluid pump 28 is active on the treatment fluid line 19 under the control of said control unit 10, to supply fluid from the treatment fluid container 20 to the secondary chamber 4 at a treatment fluid flow rate $Q_{TREAT}$. In case the pre-blood pump infusion line 21 is present, a pre-infusion pump 22, also controlled by control unit 10, may act on a segment of the pre-blood pump infusion line 21 to regulate a pre-blood pump infusion rate $Q_{PBP}$. The treatment fluid pump 28, the pre-infusion pumps 18, 22, the effluent fluid pump 17 and the post-infusion pump 27 are operatively connected to the control unit 10 which controls the pumps. The pump control may be carried out by the control unit 10 based on set values of desired flow rates through the above lines as entered by the operator or as pre-stored in a memory connected to the control unit 10.

In case the sources of the fluids are containers, such as bags as shown in FIG. 1, then scales 33, 34, 35, 36, 39 may be used to provide weight signals to the control unit 10 and thus allow the control unit 10 to determine, e.g. periodically, the actual flow rate through each line 13, 15, 19, 21, 25 and regulate the speeds of the pumps accordingly. Note that flow rate through the above lines or at least the overall weight loss rate may be determined using flow sensors 24a, 24b, 24c, 24d, 24e different from scales (schematically shown in FIG. 1). For instance, Coriolis mass flow sensors, mechanical flow sensors, electromagnetic flow sensors, volumetric flow sensors could be used in order to detect or allow detection by the control unit 10 of the actual flow rate through each of the above lines. Moreover, instead of using fluid containers 16, 20, 23, 26 the infusion fluids and/or the treatment fluid may be produced online by the apparatus 1 and then supplied to the extracorporeal blood circuit (in case of infusion fluids) and to the second chamber 4 of the treatment unit 2 (in case of treatment fluid).

Temperature sensors 29b, 29d, 29e, 29c are also present on the infusion fluid containers 16, 23, 26 and on the treatment fluid container 20 to provide temperature signals to the control unit 10.

The control unit 10 is also connected to the user interface 12, for instance a graphic user interface 12, which receives operator's inputs and displays the apparatus outputs. For instance, the graphic user interface 12 may include a touch screen, a display screen and/or hard keys for entering operator's inputs or a combination thereof.

With reference to the example of FIG. 1, a warming device 200 is associated with the apparatus 1 to form an assembly which is structured to treat blood and keep blood within certain desired temperature boundaries. The warming device 200 may be an independent device (e.g. a stand alone unit physically separated from the apparatus 1) cooperating with the apparatus 1 and—in particular—warming a portion of the extracorporeal blood circuit 100. In this case, the warming device 200 comprises its own control system 201 and its own power supply system 202 which are respectively separate from the power supply and from the control unit 10 of the apparatus 1. The control unit 10 of the extracorporeal blood treatment apparatus 1 is configured to communicate with the control system 201 of the warming device 200. Alternatively, the warming device 200 may be a component of the apparatus 1: in this case the warming device 200 is not an independent stand alone unit, but rather part of the apparatus 1.

In this second alternative, the power supply of the apparatus 1 may also serve and be connected to the warming device 200. Moreover, the control unit 10 directly controls the warming device 200. In particular the control unit 10 may be configured to execute at least two tasks: first, controlling operation of the extracorporeal blood treatment apparatus 1, and, second, controlling operation of the warming device 200.

In both cases, the warming device 200 has a heating unit 203 configured for receiving and heating a corresponding heated portion 102 of the extracorporeal blood circuit 100.

For instance, the heated portion 102 of the extracorporeal blood circuit 100 may be in the form of a substantially flat bag insertable in a heating seat provided in the heating unit 203 of the warming device 200. The flat bag presents an inlet and an outlet connected to the extracorporeal blood circuit.

Alternatively, the heated portion 102 may include a section of the tubing or a rigid cassette inserted into the heating unit 203 of the warming device 200, which heating unit 203 for instance may comprise a heating sleeve or a heating coil wound around the heated portion 102. In practice the heating unit 203 has heating elements (e.g. electric impedances, infrared emitters or other types of heating elements) configured to heat the corresponding heated portion 102 of the extracorporeal blood circuit 100.

The warming device 200 may also include a first fluid temperature sensor 204 configured for measuring at least a blood temperature at an exit of the heating unit 203 and, optionally, a second fluid temperature sensor 205 configured for measuring a further blood temperature at an entry to the heating unit 203. The warming device 200 further includes a power supply sensor 206 configured for measuring at least an actual electric power value supplied to (or absorbed by) the heating components of the warming device 200. Temperature sensor 204, sensor 205 (if present) and power supply sensor 206 are connected to the control system 201 of the blood warming device 200 or directly to the control unit 10 of the apparatus 1.

As shown in FIG. 1, the warming device 200 is associated with the extracorporeal blood circuit 100 at the blood return line 7, e.g. upstream of the bubble trap 8.

FIG. 2 schematically shows the apparatus 1 of FIG. 1 wherein the warming device 200 is associated with the blood withdrawal line 6 downstream of the blood pump 11 and upstream of the treatment unit 2.

FIG. 3 schematically shows the apparatus 1 of FIG. 1 wherein the warming device 200 is associated with the treatment fluid line 19. The heating unit 203 of the warming device 200 is configured for receiving and heating a corresponding heated portion of the treatment fluid line 19. The first fluid temperature sensor 204 is placed at the outlet of the primary chamber 3 of the treatment unit 2.

In all the embodiments the warming device 200 is configured to heat (directly or indirectly) a blood heating zone H of the extracorporeal blood circuit 100.

In the embodiments of FIGS. 1 and 2, the warming device 200 directly heats the heated portion 102 of the extracorporeal blood circuit 100. In these embodiments, the blood heating zone H therefore coincides with the heated portion 102.

In the embodiment of FIG. 3, the warming device 200 directly heats the heated portion of the treatment fluid line 19, and blood is heated by heat exchanged with the treatment fluid in the treatment unit 2. In this embodiment the blood heating zone H therefore coincides with the blood chamber of the treatment unit 2.

The control unit 10 of the apparatus 1 is configured to establish a communication with said blood warming device 200. The communication may rely on a wired or a wireless telecommunication system and is configured such as to at least allow the control unit 10 to send commands to the blood warming device 200 or to the blood warming device control system 201.

The control unit 10 is configured to perform a procedure in order to control the warming device 200 with the aim of maintaining at a desired temperature the blood flowing back to the patient P in presence of cooling effects mainly caused by infusion of fluids. In other words, the control unit 10 performs a control procedure to keep at a desired value $T_{des}$ the temperature of blood at the end 70 of the blood return line 7. In the context of the present invention, the end 70 of the blood return line 7 which is kept at the desired blood temperature $T_{des}$ is at the venous vascular access device.

Figure 4A:
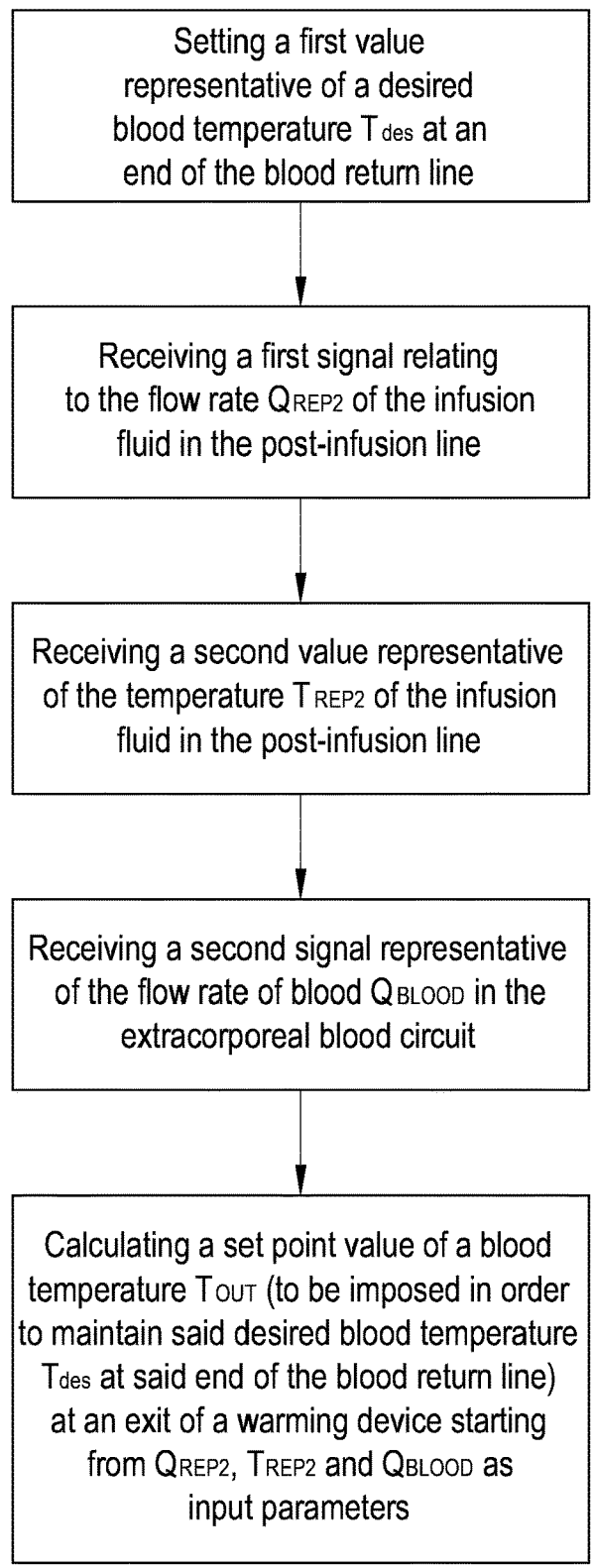
FIG. 4a is a flowchart showing a first embodiment of a control procedure according to an aspect of the invention, performable by a control unit of an apparatus, for example of the type shown in FIG. 1.

FIG. 4a shows a first flowchart of the steps the control unit 10 of apparatus 1 may be configured to execute, in accordance with a first embodiment of the procedure with reference to the apparatus 1 of FIG. 1.

Before starting the extracorporeal blood treatment, or alternatively in the course of the treatment session, a first value representative of the desired blood temperature $T_{des}$ at the end 70 of the blood return line 7 is set. The desired blood temperature $T_{des}$ is such to avoid any risk of hypothermia of the patient P under treatment (i.e. it is substantially equal to the core temperature of the patient P). The control unit 10 receives such desired blood temperature $T_{des}$.

This first value may be a fixed value (by way of example such first value may be 37.5° C.) stored in the memory of the control unit 10 or may depend on the patient P under treatment and may be entered by means of the user interface 12.

During the extracorporeal blood treatment, the control unit 10 receives, from the flow sensor 24e, a first signal relating to the post-infusion flow rate $Q_{REP2}$ of the infusion fluid in the post-infusion line 25. The control unit 10 receives, from the temperature sensor 29e, a second value which is representative of the temperature $T_{REP2}$ of the infusion fluid in said post-infusion line 25. The control unit 10 further may receive, from the blood flow sensor 30, a second signal which is representative of the blood flow rate $Q_{BLOOD}$ in the extracorporeal blood circuit 100.

Instead of the measured flows, the CPU of the control unit 10 may receive the set value of the desired post-infusion flow rate $Q_{REP2}$ of the infusion fluid in the post-infusion line 25 and the desired blood flow rate in the extracorporeal blood circuit 100 which were pre-stored in its memory. Instead of receiving the second value from the temperature sensor 29e, the temperature $T_{REP2}$ of the infusion fluid may be assumed equal to the room temperature and may be inputted in the control unit 10 by an operator by means of the user interface 12.

The control unit 10 calculates a set point value of an operating parameter to be imposed on the warming device 200 in order to maintain said desired blood temperature $T_{des}$ at said end 70 of the blood return line 7.

According to the first embodiment of the procedure, the operating parameter is the blood temperature $T_{OUT}$ at an outlet of the blood heating zone H. Referring to FIG. 1, such blood temperature $T_{OUT}$ is measured by the first fluid temperature sensor 204 at the exit of the heating unit 203 of the warming device 200.

The control unit 10 calculates the set point (blood temperature $T_{OUT}$ to be kept at the outlet of the blood heating zone H) based on the post-infusion flow rate $Q_{REP2}$ of the infusion fluid in the post-infusion line 25, on the temperature $T_{REP2}$ of the infusion fluid in said post-infusion line 25 and on the blood flow rate $Q_{BLOOD}$ in the extracorporeal blood circuit 100 as input parameters.

$$T_{OUT} = f(Q_{REP2}, T_{REP2}, Q_{BLOOD})$$

According to a variant of the first embodiment, the set point may be calculated based also on the room temperature $T_{ROOM}$ in order to take into account the heat losses to atmosphere in the extracorporeal blood circuit 100 downstream of the blood heating zone H (in the apparatus 1 of FIG. 1 this means downstream of the warming device 200).

$$T_{OUT} = f(Q_{REP2}, T_{REP2}, Q_{BLOOD}, T_{ROOM})$$

According to a possible variant of the first embodiment, the set point may also be calculated based on blood properties such as one or more in the group of: blood density, specific heat, hematocrit, total protein concentration.

Calculation of the set point of the blood temperature $T_{OUT}$ at an outlet of the blood heating zone H is performed by the control unit 10 by means of a function stored in the memory of said control unit 10 interrelating said set point with said input parameters.

The following Equation 1 expresses the temperature $T_{btrap}$ of the blood at the outlet of the bubble trap 8 as a function of the desired blood temperature $T_{des}$ taking into account the heat losses to atmosphere along the length of the blood return line 7 downstream of the bubble trap 8 and until the patient end 70 of the blood return line 7.

$$T_{btrap} = T_{ROOM} + (T_{des} - T_{ROOM}) \times \exp{\frac{p \times L_{ret}}{\rho_{blood} \times C_{pblood} \times Q_{bret}}} \quad \text{Eq. 1}$$

The following Equation 2 expresses the blood temperature $T_{OUT}$ to be kept at the outlet of the blood heating zone H (at the exit of the warming device 200) as a function of the temperature $T_{btrap}$ of the blood at the outlet of the bubble trap 8 in the condition where the said blood temperature $T_{OUT}$ is identical to the warmer set point temperature I.

$$T_{OUT} = T_w = \frac{\rho_{blood} \times C_{pblood} \times Q_{bret} \times T_{btrap} - \rho_{REF2} \times C_{pREP2} \times Q_{REP2} \times T_{REP2}}{\rho_{blood} \times C_{pblood} \times (Q_{bret} \times Q_{REP2})} \quad \text{Eq. 2}$$

with $Q_{bret} = Q_{BLOOD} + Q_{REP2}$

List of variables and parameters
$C_{pblood}$: blood specific heat (J/° C./g)
$C_{pREP2}$: infusion fluid specific heat (J/° C./g)
p: heat loss coefficient to atmosphere for return line (W/° C./m)
$L_{ret}$: length of blood return line downstream the bubble trap (m)
$\rho_{blood}$: blood density (g/ml)
$\rho_{REP2}$: infusion fluid density (g/ml
$Q_{BLOOD}$: blood flow rate (ml/min)
$Q_{bret}$: blood flow rate in the blood return line (ml/min)
$Q_{REP2}$: post infusion flow rate (ml/h)

$T_{ret}$: blood temperature at the end of blood return line (° C.)
$T_{des}$: desired blood temperature at the end of blood return line (° C.)
$T_{btrap}$: blood temperature at bubble trap outlet (° C.)
$T_{OUT}$: blood temperature at the outlet of the blood heating zone (warmer outlet) (° C.)
$T_w$: warmer set point temperature
$T_{ROOM}$: room temperature (° C.)
$T_{REP2}$: infusion fluid temperature (° C.)

The above equations are used with the following values of parameters:
$\rho_{blood}$=1.05 g/ml
$\rho_{REP2}$=1.0 g/ml
$C_{pblood}$=$C_{pREP2}$=$C_{pwater}$=4.18 J/° C./g
$T_{ROOM}$=TREP2=24° C.
$L_{ret}$=2.10 m
p=0.38 W/° C./m The desired blood temperature $T_{des}$ at the end of the blood return line 7 is set equal to 37° C.

The following table shows the set point of the blood temperature $T_{OUT}$ calculated with Eq.1 and Eq.2 for a plurality blood flow rates $Q_{BLOOD}$ and post infusion flow rates $Q_{REP2}$.

TABLE 1

| Condition | 1 | 2 | 3 | 4 | 5 | 6 |
|---|---|---|---|---|---|---|
| $Q_{BLOOD}$ (ml/min) | 100 | 100 | 200 | 200 | 300 | 300 |
| $Q_{REP2}$ (ml/h) | 800 | 1500 | 800 | 2500 | 800 | 3500 |
| $T_{btrap}$ (° C.) | 38.53 | 38.53 | 37.74 | 37.74 | 37.48 | 37.48 |
| $T_{OUT}$ = $T_w$ (° C.) | 40.98 | 43.87 | 38.80 | 41.69 | 38.17 | 41.04 |

Since the operating parameter is the blood temperature $T_{OUT}$ downstream of the warming device 200, all the heat losses upstream of the warming device 200 (caused mainly by the infusion fluids from the pre-infusion lines 15, 21 and by the treatment fluid in the treatment unit 2) need not to be taken into account in the above formula in order to calculate the set point. It follows that all the temperature sensors 29b, 29d, 29c and flow sensors 24a, 24b, 24c, 24d upstream of the blood heating zone H may also not be present for this purpose.

Referring now to the apparatus 1 of FIG. 3, it is noted that the first fluid temperature sensor 204 is placed at the outlet of the treatment unit 2, i.e. immediately downstream of the heating zone H which in this case is represented by the blood compartment or primary chamber 3 of the treatment unit 2; therefore the control unit 10 of the apparatus 1 of FIG. 1 may be configured to execute the procedure according the first embodiment (flow chart of the procedure is shown in FIG. 4a) as above described.

Concerning the apparatus of FIG. 2, the warming device 200 is placed on the blood withdrawal line 6 and downstream of the pre-infusion line 15; under these circumstances, the input parameters received by the control unit 10 are:
   from the flow sensor 24e a first signal relating to the post-infusion flow rate $Q_{REP2}$ of the infusion fluid in the post-infusion line 25;
   from the temperature sensor 29e a second value which is representative of the temperature $T_{REP2}$ of the infusion fluid in the post-infusion line 25;

from the flow sensor 24c, a third signal relating to a flow rate $Q_{TREAT}$ of a treatment fluid in the treatment fluid line 19;

from the temperature sensor 29c, a third value representative of a temperature $Q_{TREAT}$ of said treatment fluid in said treatment fluid line 19;

from the blood flow sensor 30, a second signal which is representative of the blood flow rate $Q_{BLOOD}$ in the extracorporeal blood circuit 100;

the room temperature $T_{ROOM}$.

In this way the computation of the set point of the blood temperature $T_{OUT}$ shall consider:

the cooling effect from infusion fluids downstream of the warming device 200;

the cooling effect of dialysate, involving a model of the heat exchange between blood and dialysate in the treatment unit 2;

heat losses to atmosphere in the extracorporeal blood circuit 100 downstream the warming device 200. $T_{ROOM}$ is used to take into account the heat losses to atmosphere downstream of the warming device 200 including the treatment unit 2.

Thus, for the apparatus of FIG. 2, the control unit 10 may be configured to calculate the set point of the blood temperature $T_{OUT}$ using the following general formula:

$$T_{OUT} = f(Q_{REP2}, T_{REP2}, Q_{TREAT}, T_{TREAT}, Q_{BLOOD}, T_{ROOM})$$

Please note that, although it is possible to estimate the cooling effect of dialysate without any knowledge of the characteristics of the filter of the treatment unit 2, more accurate computations are possible when these filter characteristics are taken into consideration.

In all the three apparatuses of FIGS. 1, 2 and 3, and according to the first embodiment of the procedure, the control unit 10 is configured to generate a control signal comprising a command directed to impose to the warming device 200 to operate with said operating parameter at the calculated set point.

The control unit 10 communicates the set point (blood temperature $T_{OUT}$ at the exit of the warming device 200) to the control system 201 of said warming device 200. The control system 201 receives from the first fluid temperature sensor 204 also a measured blood temperature $T_{OUT}$ at the exit of the warming device 200.

The control system 201 adjusts the electric power fed to the heating unit 203 of the warming device 200 based on said measured blood temperature $T_{OUT}$ at the exit of the warming device 200 and on said calculated set point in order to keep the measured blood temperature $T_{OUT}$ at the set point.

When the measured blood temperature $T_{OUT}$ at the exit of the warming device 200 corresponds to the set point, then the blood temperature at the end 70 of the blood return line 7 is the desired temperature $T_{des}$.

Figure 5:
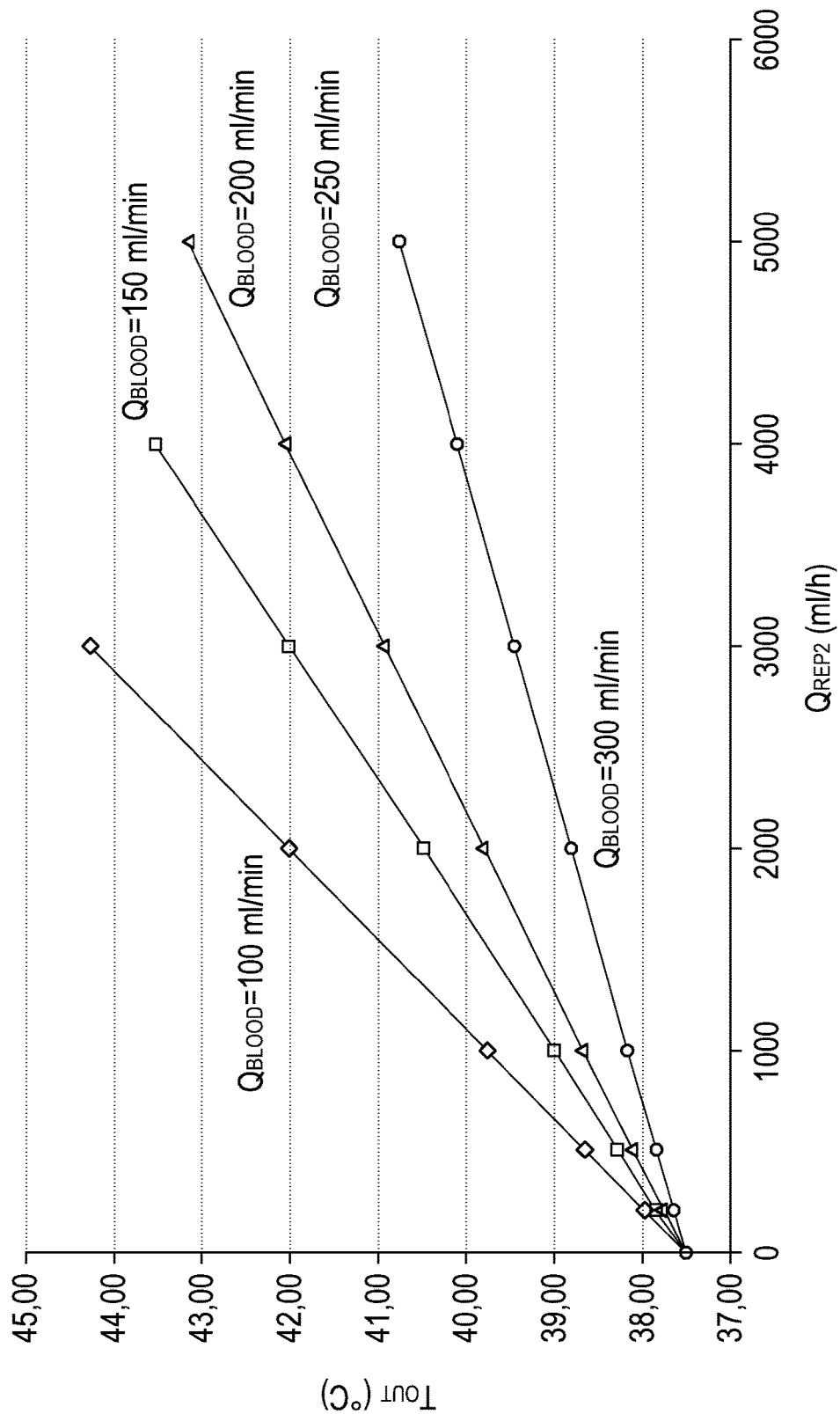
FIG. 5 is a chart showing the set point required to keep the desired blood temperature at the end of the blood return line.

FIG. 5 shows the blood temperature $T_{OUT}$ to be maintained at the exit of the warming device 200 as function of the post-infusion flow rate $Q_{REP2}$ in the post-infusion line 25 to keep the desired blood temperature $T_{des}$ at the target value of 37.5° C. when said target value has to be obtained at the outlet of the bubble trap 8 (please note that in this example the heat losses to atmosphere due to the length $L_{ret}$ of the blood return line 7 downstream of the bubble trap 8 have been neglected) and when the temperature $T_{REP2}$ of the infusion fluid is 24° C. Note that each straight line corresponds to a respective blood flow rate $Q_{BLOOD}$. For a given post-infusion flow rate $Q_{REP2}$, if the blood flow rate $Q_{BLOOD}$ increases, the blood temperature $T_{OUT}$ at the exit of the warming device 200 required to keep the target value decreases.

In the following table (table 2) the post-infusion flow rate $Q_{REP2}$ is equal to 2000 ml/h.

TABLE 2

| $Q_{BLOOD}$ (ml/min) | $T_{OUT}$ (° C.) |
|---|---|
| 100 | 42 |
| 150 | 40.5 |
| 200 | 39.7 |
| 250 | 39.3 |
| 350 | 38.8 |

In a second embodiment of the procedure, which may be adopted with the apparatuses of FIG. 1 or FIG. 2, the first fluid temperature sensor 204 is not present and the operating parameter is the electric power $P_w$ supplied to the heating unit 203 of the warming device 200 or another parameter linked to said power, such as a working temperature of said warming device 200 (by way of example, the heating plate temperature in a heating plates warming device).

In this case, the input parameters received by the control unit 10 are:

from the second fluid temperature sensor 205, the blood temperature $T_{IN}$ at the entry of the warming device 200;

from the flow sensor 24e, a first signal relating to the post-infusion flow rate $Q_{REP2}$ of the infusion fluid in the post-infusion line 25;

from the temperature sensor 29e, a second value which is representative of the temperature $T_{REP2}$ of the infusion fluid in said post-infusion line 25;

from the blood flow sensor 30, a second signal which is representative of the blood flow rate $Q_{BLOOD}$ in the extracorporeal blood circuit 100;

the room temperature $T_{ROOM}$.

$$P_w = f(T_{IN}, Q_{REP2}, T_{REP2}, Q_{BLOOD}, T_{ROOM})$$

The control unit 10 calculates the set point (electric power $P_w$ which has to be supplied to the heating unit 203) based on the post-infusion flow rate $Q_{REP2}$ of the infusion fluid in the post-infusion line 25, on the temperature $T_{REP2}$ of the infusion fluid in said post-infusion line 25 and on the blood flow rate $Q_{BLOOD}$ in the extracorporeal blood circuit 100 as input parameters and on the blood temperature $T_{IN}$ at the entry of the warming device 200. $T_{ROOM}$ is used to take into account the heat losses to atmosphere in the length of tubing downstream of the warming device 200.

Calculation of the set point is performed by the control unit 10 by means of a function stored in the memory of said control unit 10 interrelating said set point with said input parameters.

Since the operating parameter is the electric power $P_w$ supplied to the heating unit 203, and the blood temperature just upstream of the warming device 200 is known, all the heat losses upstream of the warming device 200 (caused mainly by the infusion fluids from the pre-infusion lines 15, 21 and by the treatment fluid in the treatment unit 2) need not to be taken into account in order to calculate the set point.

As far as the apparatus 1 of FIG. 2 is concerned, the warming device 200 is placed on the blood withdrawal line 6 and downstream of the pre-infusion line 15.

Figure 4B:
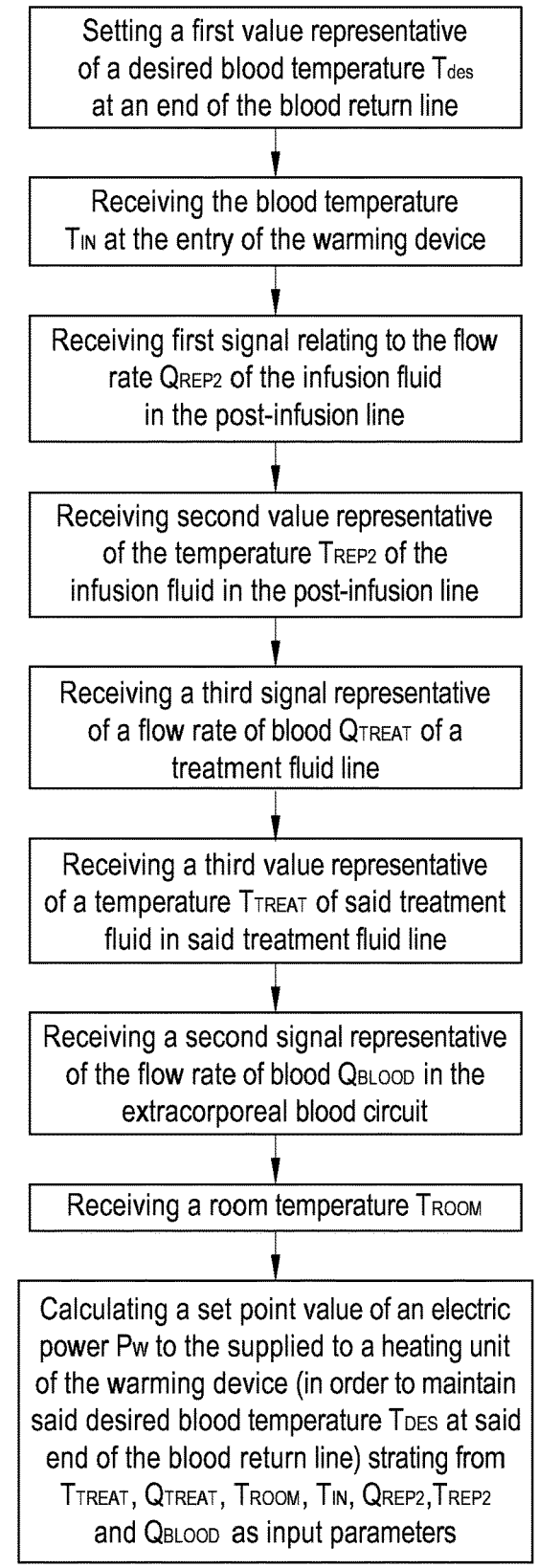
FIG. 4b is a flowchart showing a second embodiment of the control procedure according to an aspect of the invention, performable by a control unit of an apparatus, for example of the type shown in FIG. 2.

FIG. 4b shows a second flowchart of the steps the control unit 10 of apparatus 1 may be configured to execute, in accordance with the second embodiment of the procedure with reference to the apparatus 1 of FIG. 2.

The input parameters received by the control unit 10 in accordance with the second embodiment procedure are:

from the second fluid temperature sensor 205, the blood temperature $T_{IN}$ at the entry of the warming device 200;

from the flow sensor 24e a first signal relating to the post-infusion flow rate $Q_{REP2}$ of the infusion fluid in the post-infusion line 25;

from the temperature sensor 29e a second value which is representative of the temperature $T_{REP2}$ of the infusion fluid in the post-infusion line 25;

from the flow sensor 24c, a third signal relating to a flow rate $Q_{TREAT}$ of a treatment fluid in the treatment fluid line 19;

from the temperature sensor 29c, a third value representative of a temperature $T_{TREAT}$ of said treatment fluid in said treatment fluid line 19;

from the respective blood flow sensor 30, a second signal which is representative of the blood flow rate $Q_{BLOOD}$ in the extracorporeal blood circuit 100;

the room temperature $T_{ROOM}$.

In this way the computation of the set point $T_{OUT}$ shall consider:

the cooling effect from infusion fluids downstream of the warming device 200;

the cooling effect of dialysate, involving a model of the heat exchange between blood and dialysate in the treatment unit 2;

heat losses to atmosphere in the extracorporeal blood circuit 100 downstream the warming device 200. $T_{ROOM}$ is used to take into account the heat losses to atmosphere downstream of the warming device 200 including the treatment unit 2.

$$P_w = f(T_{IN}, Q_{REP2}, T_{REP2}, Q_{BLOOD}, T_{TREAT}, Q_{TREAT}, T_{ROOM})$$

The control unit 10 communicates the set point (electric power $P_w$) to the control system 201 of said warming device 200. The control system 201 adjusts the electric power fed to the heating unit 203 of the warming device 200 in order to keep it at the set point.

When the electric power $P_w$ corresponds to the set point, then the blood temperature at the end 70 of the blood return line 7 is the desired blood temperature $T_{des}$.

In a third embodiment of the procedure with the apparatus 1 of FIG. 1, the operating parameter is always the electric power Pw but the temperature at the entry of the warming device 200 is unknown (as there is no second fluid temperature sensor 205 at the entry of the warming device 200).

Figure 4C:
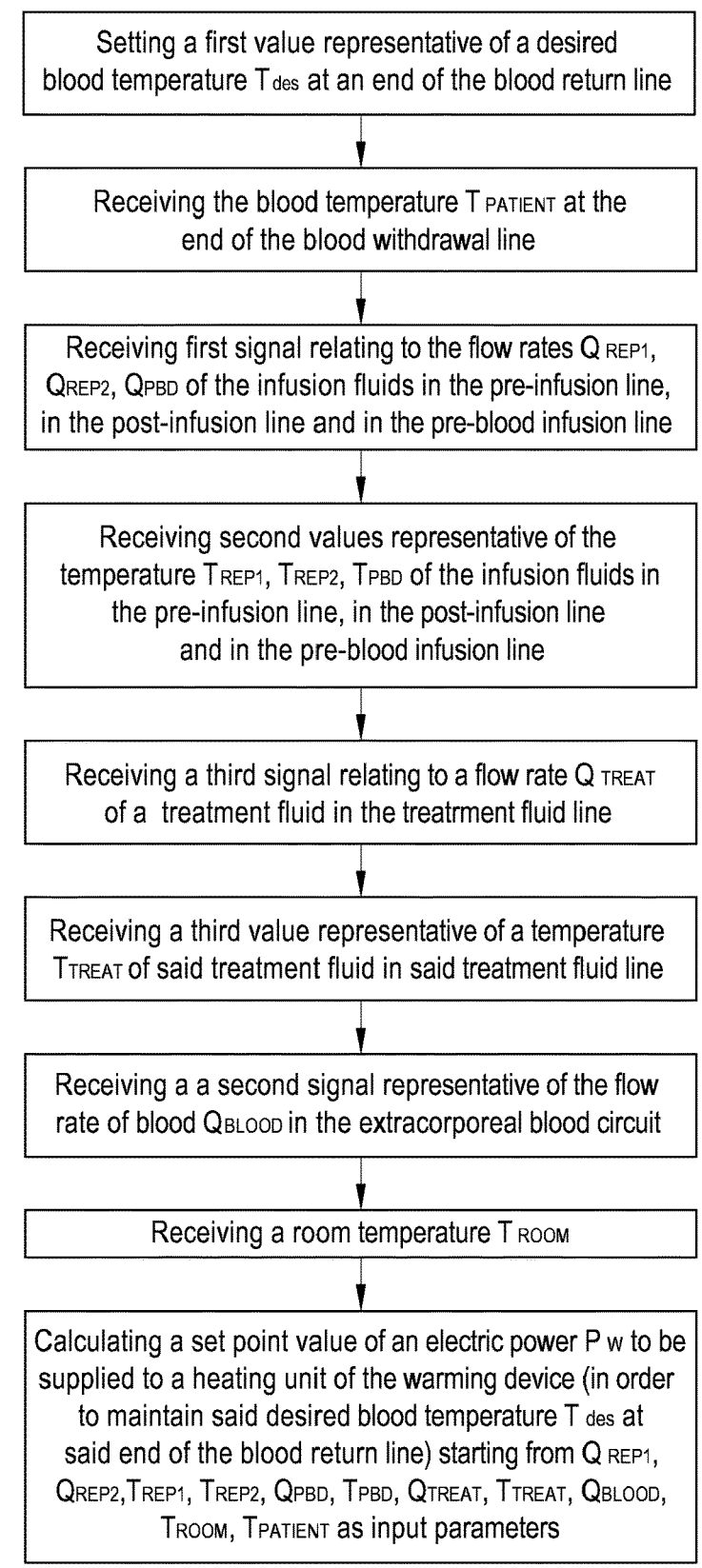
FIG. 4c is a flowchart showing a third embodiment of a control procedure according to an aspect of the invention, performable by a control unit of an apparatus, for example of the type shown in FIG. 1.

FIG. 4c shows a third flowchart of the steps the control unit 10 of apparatus 1 may be configured to execute, in accordance with the third embodiment of the procedure with reference to the apparatus 1 of FIG. 1.

The input parameters received by the control unit 10 in accordance with the procedure of the third embodiment are:

from the respective flow sensors 24e, 24b, 24d, first signals relating to the post-infusion flow rate $Q_{REP2}$ of the infusion fluid in the post-infusion line 25, the pre-infusion flow rate $Q_{REP1}$ of the infusion fluid in the pre-infusion line 15, the flow rate $Q_{PBD}$ of the infusion fluid in the pre-blood pump infusion line 21;

from the respective temperature sensors 29e, 29b, 29d, second values which are representative of the temperature $T_{REP2}$ of the infusion fluid in the post-infusion line 25, the temperature $T_{REP1}$ of the infusion fluid in the pre-infusion line 15, the temperature $T_{PBD}$ of the infusion fluid in the pre-blood pump infusion line 21;

from the flow sensor 24c, a third signal relating to a flow rate $Q_{TREAT}$ of a treatment fluid in the treatment fluid line 19;

from the temperature sensor 29c, a third value representative of a temperature $T_{TREAT}$ of said treatment fluid in said treatment fluid line 19;

from the blood flow sensor 30, a second signal which is representative of the blood flow rate $Q_{BLOOD}$ in the extracorporeal blood circuit 100;

the temperature $T_{PATIENT}$ of blood at the end 60 of the blood withdrawal line 6 (which is the core temperature of the patient P and may be set at about 37.5° C.)

the room temperature $T_{ROOM}$.

$$P_w = f(Q_{REP1}, Q_{REP2}, T_{REP1}, T_{REP2}, Q_{PBD}, T_{PBP}, Q_{TREAT}, T_{TREAT}, Q_{BLOOD}, T_{PATIENT}, T_{ROOM})$$

The control unit 10 calculates the set point (electric power $P_w$ to be supplied to the heating unit 203 of the warming device 200) based on said input parameters. $T_{ROOM}$ is used to take into account the heat losses to atmosphere in the length of tubing downstream of the warming device 200.

Calculation of the set point is performed by the control unit 10 by means of a function stored in the memory of said control unit 10 interrelating said set point with said input parameters.

Since the temperature at the entry of the warming device 200 is unknown and since the operating parameter (power provided by the warming device 200) is related to the amount of heat delivered to the blood at the heating zone H, all the heat losses upstream and downstream of the warming device 200 and also the blood temperature $T_{PATIENT}$ at the end 60 of the blood withdrawal line 6 (which is the core temperature of the patient P) should be taken into account in order to calculate the set point which provides the desired blood temperature $T_{des}$ at the end 70 of the blood return line 7.

As a general rule, if a blood temperature sensor in the blood treatment circuit is present, the calculation may be independent of what happens upstream of said blood temperature sensor.

The apparatus 1 may further comprise a communication device 300 connected to the control unit 10. The communication device 300 may also be part of the user interface 12. By means of the communication device 300, data from the control unit 10 and/or from the control system 201 of the warming device 200 may be communicated to the operator.

The control unit 10 may be configured to communicate by means of said communication device 300 the set point to the operator.

If the warming device 200 is a component of the apparatus 1 and the warming device 200 is connected to the control unit 10, the control unit 10 directly controls the warming device 200 and the set point may be displayed by the communication device 300. The control unit 10 recalculates the set point either periodically or when a change to at least one of the input parameters occurs and, if a new set point is calculated, automatically sends a command directed to impose to the warming device 200 to operate with said operating parameter at the new set point.

For instance, if infusion in one or more of the infusion lines 15, 21, 25 is stopped (e.g. in order to change an infusion fluid container 16, 23, 26), the control unit 10 reduces the set point in order to keep the desired blood temperature $T_{des}$.

According to an embodiment of the apparatus 1 in which the warming device 200 is not connected to the control unit 10 (e.g. because the warming device 200 is an independent device with respect to the apparatus 1), the set point calculated by the control unit 10 is displayed to the operator and the operator inputs said set point into the warming device 200 (e.g. by means of a user interface, not shown, of the warming device 200). The control unit 10 recalculates the set point either periodically or when a change to at least one of the input parameters occurs and, if a new set point is calculated, warns the operator (e.g. by means of an a visual and/or acoustic signal) to input said new set point into the warming device 200.

According to a variant of the apparatus 1 in which the warming device 200 is not connected to the control unit 10, the control unit 10 may warn the operator also in case of stop of one or more of the infusion fluids.

The control unit 10 may be further configured to take into account a maximum set point in order to prevent patient P over-warming and/or any blood damage. This maximum set point could be exceeded if, for instance, the operator makes a mistake when inputting the set point into the warming device 200 or in case of prolonged stop of infusion (if the warming device 200 is not controlled by the control unit 10). This maximum set point could also be exceeded in case of failure of one or more sensors (even if the control unit 10 controls the warming device 200).

In particular, the control unit 10 may be configured to receive the maximum set point (e.g. set by the operator by means of the user interface 12) and to compare the calculated set point with the maximum set point.

The maximum set point may be a function of the weight of the patient P and/or of flow settings. In this case, the control unit 10 computes also the maximum set point.

If the calculated set point exceeds the maximum set point and the warming device 200 is controlled by the control unit 10, said control unit 10 automatically sends a command directed to impose to the warming device 200 to operate with said operating parameter at the maximum set point.

If the calculated set point exceeds the maximum set point and the warming device 200 is not controlled by the control unit 10, said control unit 10 is configured to send a warning message (e.g. a visual and/or acoustic signal) to the operator by means of the communication device 300.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An extracorporeal blood treatment apparatus, comprising:
    an extracorporeal blood circuit having a treatment unit, a blood withdrawal line connected to a blood inlet of the treatment unit, and a blood return line connected to a blood outlet of the treatment unit;
    a blood pump configured for controlling blood flow rate flowing through at least one of said blood withdrawal line and blood return line;
    an infusion line connected to the extracorporeal blood circuit, wherein the infusion line is connected to the extracorporeal blood circuit at a junction point positioned downstream of a blood heating zone;
    a control unit configured to execute the following procedure:
        receive a first value representative of a desired blood temperature at an end of the blood return line, wherein the end of the blood return line is configured to be connected to a venous vascular access of a patient;
        receive a first signal relating to a flow rate of an infusion fluid in said infusion line;
        calculate a set point of an operating parameter to be imposed on a warming device configured to heat the blood heating zone of the extracorporeal blood circuit in order to maintain said desired blood temperature at said end of the blood return line;
        wherein the set point is calculated based on input parameters comprising:
            at least the first value representative of the desired blood temperature, and
            at least one of:
                the first signal, and
                a second value representative of a temperature of said infusion fluid in said infusion line.

2. Apparatus according to claim 1, wherein the control unit is further configured to receive a second signal relating to the blood flow rate in the extracorporeal blood circuit, wherein the input parameters comprise said second signal.

3. Apparatus according to claim 1, wherein the junction point is positioned between the blood heating zone and said end of the blood return line.

4. Apparatus according to claim 1, wherein the apparatus further comprises a treatment fluid line connected to the treatment unit.

5. Apparatus according to claim 4, wherein the control unit is further configured to:
    receive a third signal relating to a treatment fluid flow rate in said treatment fluid line; and
    receive a third value representative of a temperature of said treatment fluid in said treatment fluid line;
    wherein the input parameters comprise the third signal and the third value representative of the temperature of the treatment fluid.

6. Apparatus according to claim 5, wherein the infusion line comprises one infusion line of a plurality of infusion lines connected to the extracorporeal blood circuit and the first signal comprises one first signal of a plurality of first signals, wherein each first signal of the plurality of first signals relates to a flow rate of an infusion fluid in one infusion line of the plurality of infusion lines;
    wherein the control unit is configured to receive the plurality of first signals;
    and wherein the input parameters further comprise:
        one or more first signals of the plurality of first signals, and
        one or more temperatures of the infusion fluid in one or more infusion lines of the plurality of infusion lines connected to the extracorporeal blood circuit downstream of the blood heating zone.

7. Apparatus according to claim 5, wherein the infusion line comprises a plurality of infusion lines and wherein one or more infusion lines of the plurality of infusion lines are connected to the extracorporeal blood circuit upstream of the blood heating zone;
    and wherein the input parameters further comprise:
        one or more first signals of the plurality of first signals relating to a flow rate of the infusion fluid in the one or more infusion lines connected to the extracorporeal blood circuit upstream of the blood heating zone, and one or more temperatures of the infusion fluid in the one or more infusion lines connected to the extracorporeal blood circuit upstream of the blood heating zone.

8. Apparatus according to claim 1, wherein the operating parameter is representative of the blood temperature at an outlet of the blood heating zone.

9. Apparatus according to claim 1, wherein the blood heating zone is a portion of the extracorporeal blood circuit positioned on the blood return line.

10. Apparatus according to claim 1, comprising the warming device which is configured to heat the blood heating zone.

11. Apparatus according to claim 1, wherein the warming device is connected to the control unit and the control unit is configured to generate a control signal comprising a command configured to cause the warming device to operate with said operating parameter at the calculated set point.

12. Apparatus according to claim 1, comprising a fluid temperature sensor configured to measure a blood temperature at the outlet of the blood heating zone and to issue a corresponding measurement signal; wherein the operating parameter is the blood temperature at the outlet of the blood heating zone; wherein the control unit is configured to perform a feedback control on the warming device, said feedback control comprising regulating electric power fed to a heating unit of the warming device or regulating a temperature of a part of the warming device based on a said measurement signal and on said calculated set point.

13. Apparatus according to claim 1, comprising a warming device, wherein the warming device comprises a warming device control system separate from the control unit;
wherein the warming device control system is configured to receive a control signal from the control unit, the control signal comprising a command configured to cause the warming device to operate with said operating parameter at the calculated set point.

14. Apparatus according to claim 13, wherein the warming device comprises a fluid temperature sensor configured to measure a blood temperature at the outlet of the blood heating zone and to issue a corresponding measurement signal; wherein the operating parameter is the blood temperature at the outlet of the blood heating zone; wherein the warming device control system is configured to perform a feedback control, said feedback control comprising regulating electric power fed to a heating unit of the warming device based on said measurement signal and on said calculated set point imposed by said command.

15. Apparatus according to claim 1, wherein the apparatus comprises a warming device, wherein the warming device comprises a warming device control system separate from the control unit;
wherein the apparatus comprises a communication device configured to communicate the calculated set point to an operator;
wherein the warming device control system is configured to receive said calculated set point and to cause the warming device to operate with said operating parameter at the calculated set point.

* * * * *